US009501919B2

(12) United States Patent      (10) Patent No.: US 9,501,919 B2
Laett et al.      (45) Date of Patent: Nov. 22, 2016

(54) METHOD AND SYSTEM FOR MONITORING THE ACTIVITY OF A SUBJECT WITHIN SPATIAL TEMPORAL AND/OR BEHAVIORAL PARAMETERS

(76) Inventors: Elisabeth Laett, Montreal (CA); Laurent Ruhlmann, Montreal (CA)

( * ) Notice: Subject to any disclaimer, the term of this patent is extended or adjusted under 35 U.S.C. 154(b) by 927 days.

(21) Appl. No.: 13/418,077

(22) Filed: Mar. 12, 2012

(65) Prior Publication Data

US 2012/0229634 A1     Sep. 13, 2012

Related U.S. Application Data

(60) Provisional application No. 61/452,000, filed on Mar. 11, 2011.

(51) Int. Cl.
*G08B 21/04* (2006.01)

(52) U.S. Cl.
CPC ......... *G08B 21/0476* (2013.01); *G08B 21/043* (2013.01); *G08B 21/0423* (2013.01)

(58) Field of Classification Search
CPC ............ G08B 21/0423; G08B 21/043; G08B 21/0476
See application file for complete search history.

(56) References Cited

U.S. PATENT DOCUMENTS

| | | | | |
|---|---|---|---|---|
| 5,846,086 | A * | 12/1998 | Bizzi et al. | 434/247 |
| 6,820,112 | B1 * | 11/2004 | Matsuda et al. | 709/203 |
| 7,412,396 | B1 * | 8/2008 | Haq | 705/2 |
| 2002/0128746 | A1 * | 9/2002 | Boies et al. | 700/245 |
| 2002/0146672 | A1 * | 10/2002 | Burdea et al. | 434/258 |
| 2002/0165733 | A1 * | 11/2002 | Pulkkinen et al. | 705/2 |
| 2003/0058341 | A1 * | 3/2003 | Brodsky | G06K 9/00335 348/169 |
| 2003/0177177 | A1 * | 9/2003 | Oka et al. | 709/203 |
| 2004/0243447 | A1 * | 12/2004 | Kamiyama et al. | 705/3 |
| 2005/0131663 | A1 * | 6/2005 | Bangs et al. | 703/11 |
| 2005/0172398 | A1 * | 8/2005 | Smith et al. | 5/81.1 R |
| 2006/0028350 | A1 * | 2/2006 | Bhai | 340/666 |
| 2006/0049936 | A1 * | 3/2006 | Collins et al. | 340/539.11 |
| 2007/0003915 | A1 * | 1/2007 | Templeman | 434/247 |
| 2007/0032733 | A1 * | 2/2007 | Burton | 600/509 |
| 2007/0132597 | A1 * | 6/2007 | Rodgers | 340/573.1 |
| 2007/0255115 | A1 * | 11/2007 | Anglin et al. | 600/300 |
| 2007/0276501 | A1 * | 11/2007 | Betz et al. | 623/17.16 |
| 2008/0124687 | A1 * | 5/2008 | Post | 434/219 |
| 2008/0146302 | A1 * | 6/2008 | Olsen et al. | 463/7 |
| 2008/0303830 | A1 * | 12/2008 | Fleury et al. | 345/473 |
| 2009/0033737 | A1 * | 2/2009 | Goose et al. | 348/14.07 |
| 2009/0119843 | A1 * | 5/2009 | Rodgers et al. | 5/611 |
| 2009/0144148 | A1 * | 6/2009 | Jung et al. | 705/14 |
| 2009/0164917 | A1 * | 6/2009 | Kelly | 715/757 |
| 2009/0271347 | A1 * | 10/2009 | Hyde et al. | 706/46 |
| 2010/0083112 | A1 * | 4/2010 | Dawson et al. | 715/706 |

(Continued)

*Primary Examiner* — Peter D Le
(74) *Attorney, Agent, or Firm* — Equinox IP; Franz Bonsang

(57) ABSTRACT

Methods and systems for monitoring a subject within a defined spatial environment in order to signal the activity status of subject within the environment to a remote user comprise providing a virtual representation and a virtual model of the subject and the environment respectively. The foregoing can be performed by a camera which is linked to a controller for translating the captured images into virtual versions. The activities of the subject are assigned activity statuses. Hence, assessing the activities of the virtual subject within the virtual environment and comparing this activity to previously assigned statuses provides for determining the activity status of the subject within the environment and communicating this information to a remote user via an interface linked to the controller.

11 Claims, 9 Drawing Sheets

(56) References Cited

U.S. PATENT DOCUMENTS

| | | | |
|---|---|---|---|
| 2010/0169798 A1* | 7/2010 | Hyndman et al. | 715/757 |
| 2010/0217619 A1* | 8/2010 | Cox et al. | 705/2 |
| 2010/0299618 A1* | 11/2010 | Pare | 715/757 |
| 2011/0082445 A1* | 4/2011 | Van der Helm | A61M 5/14244 604/890.1 |
| 2011/0098109 A1* | 4/2011 | Leake et al. | 463/30 |
| 2012/0139899 A1* | 6/2012 | Winchester | 345/419 |
| 2013/0300573 A1* | 11/2013 | Brown et al. | 340/870.01 |

* cited by examiner

| Incident | Time to detect | Possible complications | Possible Intervention | Estimated Cost Impact |
|---|---|---|---|---|
| MINOR FALL | <2-4 hrs | No Complications | A visit form a care attendant | Less than $20 |
| | <5-23 hrs. | Formation of pressure sore, complications of missing medicine | Requires medical intervention to treat pressure sore May require physician or urgent care visit | Average urgent care/ER visit cost $560 Average cost for treatment of pressure is $4,700 to $11,000 |
| | <24-47 hrs. | Dehydration and additional complications for missing medicine | Requires extended emergency room visit or hospital stay | Average hospitalization cost for older adults is $17,734 Patient over 75 admitted after an accident (most often a fall) occupy a hospital bed for an average of 18 days |
| | >48 hrs. | Serious complications likely causing alterations in living conditions | One month stay in skilled nursing facility | Hospitalization followed by 1 month rehab in skilled nursing facility Average skilled nursing cost is $6,500 per month |

Figure 1

METHOD AND SYSTEM FOR MONITORING THE ACTIVITY OF A SUBJECT WITHIN SPATIAL TEMPORAL AND/OR BEHAVIORAL PARAMETERS

CROSS-REFERENCE TO RELATED APPLICATIONS

The present application claims priority of U.S. Provisional Application for Patent No. 61/452,000 filed on Mar. 11, 2011, the contents of which is incorporated by reference herein in its entirety.

TECHNICAL FIELD

The present disclosure relates to a method and system for monitoring the activity of a subject within spatial, temporal and/or behavioral parameters. More specifically, but not exclusively, the present disclosure relates to a method and a system of monitoring a subject within a defined spatial environment in order to signal the activity status of this subject within the environment to a remote user without requiring direct observation.

BACKGROUND

The average age of the world's population is increasing at an unprecedented rate. The number of people worldwide age 65 and older is estimated at 506 million as of midyear 2008; by 2040, that number will hit 1.3 billion. Thus, in just over 30 years, the proportion of older people will double from 7 percent to 14 percent of the total world population, according to a new report, "An Aging World: 2008."

Subjects in their own residences as well as those in independent living facilities (ILF), Assisted Living Facilities (ALF) and staffed nursing facilities (SNF) (here in after referred to as residences) can benefit from or may require regular or additional supervision from a caretaker to provide early detection of changes in behavior or normal patterns of daily activities that may indicate or coincide with changes in their health or activities that can lead to injuries from accident. This monitoring requirement is particularly acute for people that suffer from more advanced cognitive diseases such as dementia or Alzheimer's. For instance each year, an average nursing home with 100 beds reports 100 to 200 falls (Rubenstein L Z. Preventing falls in the nursing home. Journal of the American Medical Association 1997; 2780: 595-6). A significant number of older adults living in residence homes die each year from fall-related injuries. Those who experience non-fatal falls can suffer injuries, have difficulty getting around and have a reduced quality of life (Rubenstein L Z, Josephson K R, Robbins A S Falls in the nursing home. Annals of Internal Medicine 1994; 121:442-51.) Specifically, 10% to 20% of nursing home falls cause serious injuries; 2% to 6% cause fractures. According to figures of the US department of Health—Center for Disease Control and prevention, in 2003, 1.5 million people aged 65 years and older lived in nursing homes. If the current rates continue, by 2030 this number will rise to about 3 million. About 5% of adults 65 and older live in nursing homes, but nursing home residents account for about 20% of deaths from falls in this age group. As many as 3 out of 4 nursing home residents fall each year which is twice the rate of older adults who are not in health care or retirement facilities. Moreover, the average falls per person per year is 2.6. About 35% of fall injuries occur among residents with reduced mobility. Falls result in disability, functional decline and reduced quality of life and the fear of falling can cause further loss of function, depression, feelings of helplessness, and social isolation.

The challenge in caring for clients is the enormous burden of visually monitoring each client. The challenge primarily comes when an individual falls in a room or bathroom and there is no one watching them during this time. Due to overburdened staff in most facilities it is almost impossible to determine what an effective response is required until you have visually identified the situation. Technology can help to fill gaps left by a limited and budget constrained care-giving workforce and dispersed families.

Falling can be a sign of other health problems. People in nursing homes are generally frailer than other adults living in the community. They are generally older, have more chronic conditions, and have difficulty walking. They also tend to have problems with thinking or memory, to have difficulty with activities of daily living, and need help getting around or taking care of themselves. According to the Journal of the American Geriatrics Society all of these factors are linked to falling. Outlined in table 1 (see FIG. 1) are the potential cost impacts of a subject under care falling (table 1 from Ziegler Senior living and finance strategy conference 2009 Optimizing technology investments: best care for best cost presentation).

Caregivers of clients suffering from Alzheimer's disease and related dementia diseases face numerous additional challenges. In particular such clients need more frequent monitoring to ensure their well-being and that they do not harm themselves. With limited time and/or client to caregiver ratios increasing, it is difficult to monitor their activity constantly and consistently.

This visual identification is time and resource heavy for caregivers as well as larger scale nursing homes and hospital environments. Additionally family members may also want to monitor the general well-being of an ailing family member may be constrained by distance.

Client monitoring has been attempted with video yet this approach still requires significant human interaction and it is often resisted or refused as personal invasion of privacy. Many care facilities would not video monitor a patient without their explicit permission. Even if they do receive permission, it only nominally lowers the 1-1 ratio of patient care required for monitoring and analysis.

Various GPS monitoring systems, RF ID systems and personal emergency response devices based on accelerometer technology have been developed to track or monitor the whereabouts of clients. For example, certain products include personal response devices worn on a wristband or pendant and having a signaling button which allows the person in need to summon help at any time, without speech from trained personnel. Various other products provide alarm signaling devices that can be attached to the patient's body. However, some of these products have significant disadvantages; namely, they sometimes require the cognizance of the patient to ask for help which is not always possible with patients suffering from dementia and the like inflictions. Other disadvantages are the ability of the patient to communicate with a dispatch center. Still other products include sensors in various rooms for sensing the presence or absence of the subject in a given room. Yet, these systems often do not provide sufficient information required by caregivers.

There thus remains a need to monitor the activity risk without direct observation of a subject in order to better track, react faster to, and even predict health-impairing situations before or shortly after they occur.

OBJECTS

An object of the present disclosure is to provide a method and/or a system for monitoring the activity of a subject without requiring direct observation.

An object of the present disclosure is to provide a method and/or a system for monitoring the activity of a subject without requiring the subject to wear a tracking-specific device.

An object of the present disclosure is to provide a method and/or a system for monitoring the activity status of a subject within spatial and temporal parameters.

An object of the present disclosure is to provide a method and/or a system of monitoring a subject within a defined spatial and temporal environment in order to signal the activity status of the subject within the environment to a remote user without requiring direct observation.

An object of the present disclosure is to provide a method of monitoring a subject within a defined spatial environment in order to signal the activity status of subject within the environment to a remote user.

An object of the present disclosure is to provide a system for monitoring a subject within a spatial environment in order to signal the activity status of the subject within the environment to a remote user.

An object of the present disclosure is to provide an information processing system.

SUMMARY

In accordance with an aspect of the disclosure there is provided a method of monitoring a subject within a defined spatial environment in order to signal the activity status of subject within the environment to a remote user, the method comprising:

providing a virtual representation of the subject;

providing a virtual model of the environment;

assigning a given activity status to a given activity of the subject;

assessing the real-time activity of the virtual representation of the subject within the virtual model of the environment; and comparing this activity to the assigned activity status for determining an activity status in real-time.

In accordance with an aspect of the disclosure there is provided a system for monitoring a subject within a spatial environment in order to signal the activity status of the subject within the environment to a remote user, the system comprising:

a camera for capturing the image of the environment and the image of the subject therein;

a controller in communication with the camera for receiving the captured image of the environment and the subject and for translating the captured images into a virtual model of the environment and into a virtual representation of the subject, the controller comprising a database of assigned activity statuses for given activities of the subject within the environment, the controller providing for assessing the real-time activity of the virtual representation of the subject within the virtual model of the environment and for comparing this activity to the assigned activity statuses thereby determining an activity status in real-time; and an interface in communication with the controller for receiving and communicating to a user the activity status of subject in real-time.

In accordance with an aspect of the disclosure there is provided an information processing system comprising:

a main controller; and a plurality of monitoring systems disclosed herein, wherein each controller thereof is in communication with the main controller for transmitting information regarding:

(a) the assessment of the real-time activity of the virtual representation of the subject within the virtual model of the environment; (b) the receipt of the activity status by the interface, and (c) any response to an activity status.

In an embodiment, the present disclosure provides 3D motion capture of a subject to assist in the intelligent monitoring and effective response determination for professional and non-professional caregivers of clients requiring individual surveillance.

In an embodiment, the present disclosure uses 3D motion capture systems that translate a subject within an enclosed setting to a computer generated skeletal rig without requiring a marker system.

In an embodiment, the present disclosure provides grid mapping of a 3D space thereby providing for monitoring the activity of a subject without direct physical observation thus respecting the privacy of the subject.

In an embodiment, the present disclosure provides motion capture of 3D data to track the activity of a subject who requires monitoring and they could have a physical and/or mental affliction such as reduced mobility or reduced cognitive functions. In an embodiment, there is provided a system for identifying irregular and/or alarming activity, providing automated voice guidance and/or alarm escalation to a remote monitoring user such as a caregiver thereby signaling when a state of escalated emergency is about to occur or is occurring or has occurred.

In an embodiment, there is provided a method that uses real-time motion capture with contextual environmental alarms that covers three dimensions, that is time, physical position and virtual terrain space in order to more effectively monitor, detect an incident whether it be a behavior or an event that poses a predetermined degree of risk to a subject all the while providing a signal to either prevent or to respond to this behavioral risk. For example, the event can be a fall, the risk can be standing within zone that does not allow the patient to properly support themselves and potentially provide fall prevention for a client.

In an embodiment, there is provided a 24 hour monitoring system for secure and cost effective long term care of a subject. The subject is monitored through the use of motion capture, within a defined environment providing real time information as to the subject's activities over the course of a 24 hour cycle, such as their position in the environment and the activity that they are undertaking at any moment in time. The method provides the use of real-time motion capture to create a 3-D avatar that interacts with contextual environmental alarms that cover these movements over cycles of time, physical position and position within the terrain space. In an embodiment, there is provided a motion capture system using a video camera or cameras to capture motion in order to capture the skeletal rig of a given subject and to tracks its movement within a grid map of a room. The camera or cameras are linked to a controller in order to receive information regarding the position of the subject within the grid, the range of motion of the subject within the grid and the time of the day that an event occurs within the grid. This system can be used for example to monitor a patient suffering from dementia, such as Alzheimer's, twenty-four hours a day, seven days a week with minimal privacy intervention and without the need to have someone constantly directly intervening for visual monitoring. In an embodiment, the controller is configured to notify the person monitoring the subject of the subject's activity or state within the grid, for example, four different signals can be associated with four different levels of activity such as: Level 1: normal activity; Level 2: abnormal activity (i.e. a abnormal event has occurred); Level 3: Activity within the grid is now serious or dangerous; Level 4: Activity level has generated multiple alarms and immediate response is required, In one example, when the subject is in Level 3 or 4, an alarm such as (e.g. a pre-recorded voice message) is produced to notify the subject that their behavior should be modified. For example, the controller can be programmed to qualify as normal a horizontal position of the skeletal rig during certain hours of the day (i.e. during normal sleep hours). If the position of the rig changes during those hours, this would be considered an abnormal event and the alarm would be triggered. For example, during sleep, the subject may suddenly move to an upright position on their bed at a certain moment in the night because they are disoriented, the voice alarm could tell them the time and that they should not get up and return to sleep. Of course, a variety of sounds, signals and voice activated alarms can be used within the context of this innovation. Furthermore, various positions and ranges of motion can correspond to different levels of activity or states in relation to the time of day. Providing various bundles of time-dependent activity (position and/or motion) that can be categorized within different levels (again depending on the time or time range they occur in), alleviate the person monitoring the subject from having to actually observe a remote screen with a live feed video.

The person monitoring the subject can use a handheld unit such as a smart device, phone or portable computer, for example, in order to receive real time information of the subject's activity level displayed through and ALARM code interface. The unit would merely indicate the activity level of the subject and not display at any level the individual video capture that is being analyzed for activity level. In another embodiment with correct level permissions the unit could display the video that is being analyzed for activity level, A variety of buzzers, signals and alarms can also be contemplated in order to bring to the monitor's attention that a higher level event has occurred or that an urgent response is needed.

In an embodiment, the method also provides for gesture recognition, and voice recognition.

Other objects, advantages and features of the present disclosure will become more apparent upon reading of the following non-restrictive description of non-limiting illustrative embodiments thereof, given by way of example only with reference to the accompanying drawings.

BRIEF DESCRIPTION OF THE DRAWINGS

In the appended drawings, where like reference numerals denote like elements throughout and in where:

FIG. 1 shows a table of the potential cost impacts of a human subject under care falling;

DETAILED DESCRIPTION OF ILLUSTRATIVE EMBODIMENTS

Generally stated and in accordance with an embodiment of the present disclosure, there is provided a method and a system for motion capture of a subject within a defined environment. The subject and defined environment are respectively translated into computer models for example; the subject may be translated into a countered representation, a skeletal rig as well as an avatar based on the rig. The defined environment may be translated into a grid map. Given activities of the subject are assigned activity statuses dependent on the movement of the subject (including the range of motion), the position of the subject within the defined environment as well as the current time of the movement and/or position. A controller therefore assesses the activity of the rig within the grid map and compares this activity to the predetermined activities, when a match between a real-time skeletal rig activity with a predetermined activity is made then the activity status of the rig is ascertained. Therefore, groups of activities are classified and assigned an activity status from normal to dangerous or any like status codification. The controller is in communication with a remote user interface and transmits information regarding the real-time activity status of the skeletal rig to the user interface. The activity status can also trigger an alarm signal in order to directly warn the subject and one or more remote users.

With reference, to the appended Figures, non-restrictive illustrative embodiments will be herein described so as to further exemplify the disclosure only and by no means limit the scope thereof.

Figure 2:
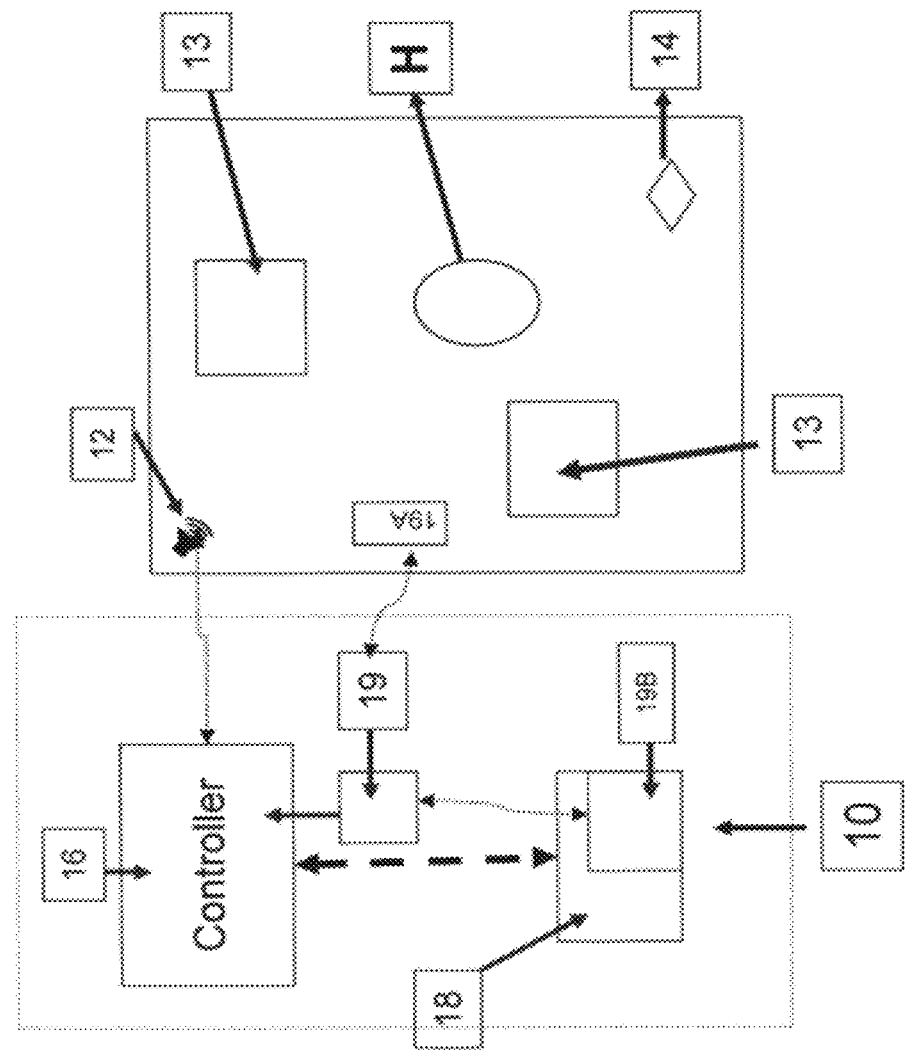
FIG. 2 is a schematic representation of the system for monitoring the activity status of a human subject within spatial and temporal parameters in accordance with a non-restrictive illustrative embodiment of the present disclosure.
Figure 3:
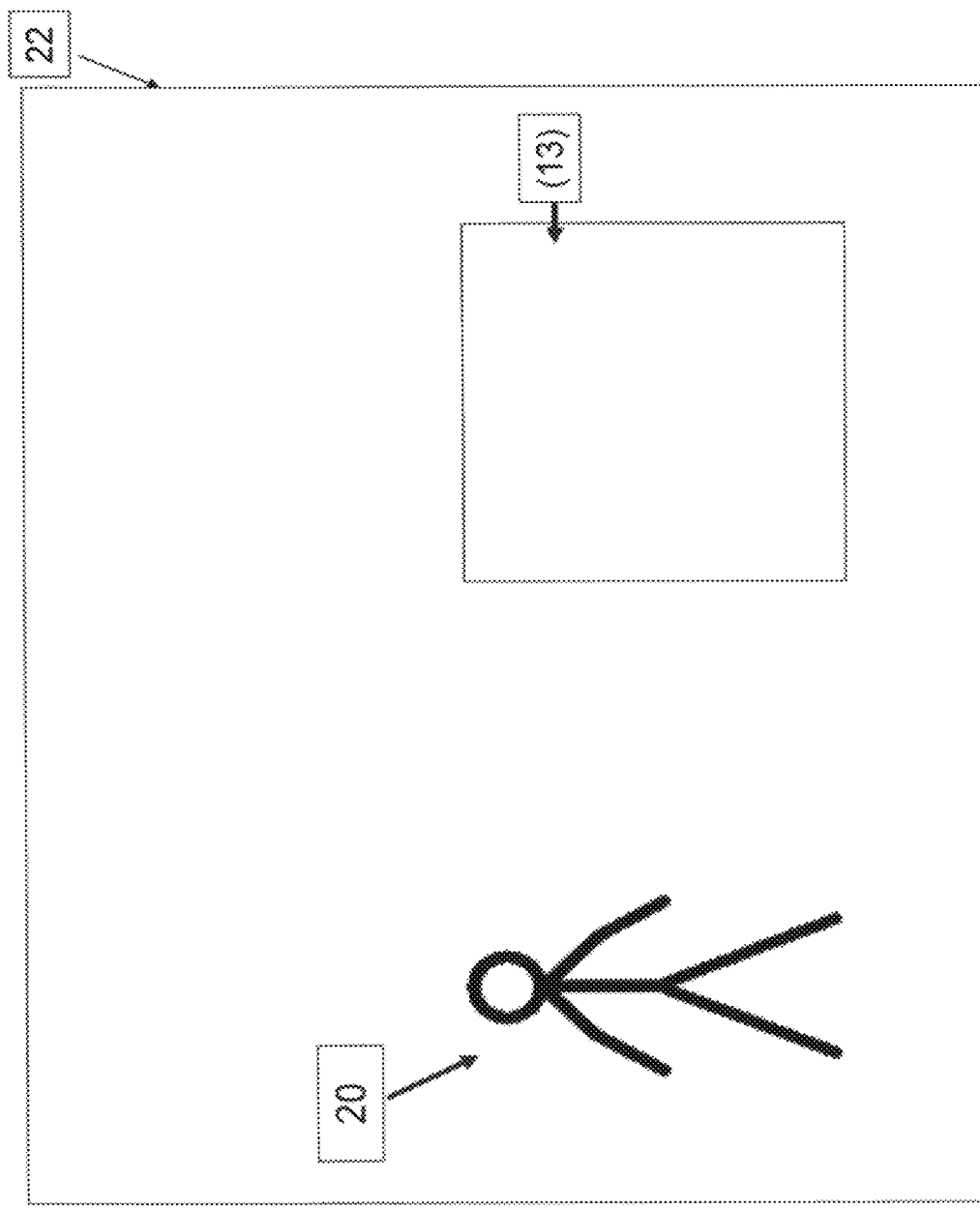
FIG. 3 is a schematic representation of a skeletal rig within a grid map provided by the system of FIG. 2.

FIG. 2 shows the system 10 for monitoring the activity status of a subject within spatial parameters comprising a camera 12 positioned within a defined spatial environment 14 such as a room. The camera can support the acquisition of depth images. The camera 12 is in communication with a controller 16 (such as a data processor, a computer and the like) which is in further communication with an interface device 18 and an alarm output 19 in the form of two devices, one alarm device 19A is positioned within the environment 14 (such as speakers) and the other device 19B forms part of the remote interface 18. Of course, both alarm device 19A and 19B can provide two-way communication as is well known in the art. Of course, the skilled artisan will readily appreciate that the controller 16 and the remote interface 18 can be provided by a single device such as a computer for example. In another embodiment, the remote interface 18 is an auxiliary unit linked to the computer 16. The camera 12 records the environment 14 as well as a subject H within this environment 14. As shown in FIG. 3, the controller 16 respectively translates the subject H into a computed representation such as a skeletal rig 20 and the environment 14 into a computed model such as a grid map 22. The subject H may be represented by other computer generated virtual structures and hence, instead of a rig, a contoured outline of the subject can be provided. Furthermore, the rig can provide for building an avatar.

As the subject H moves within the environment 14 this movement is simultaneously in real-time translated to the skeletal rig 20 which is caused to replicate the subject's movement within the virtual environment (i.e. the grid map 22). The controller thereby assesses the activity of the rig 20 within the map 22 which is a copy of the activity of the subject H within the environment 14.

Figure 4:
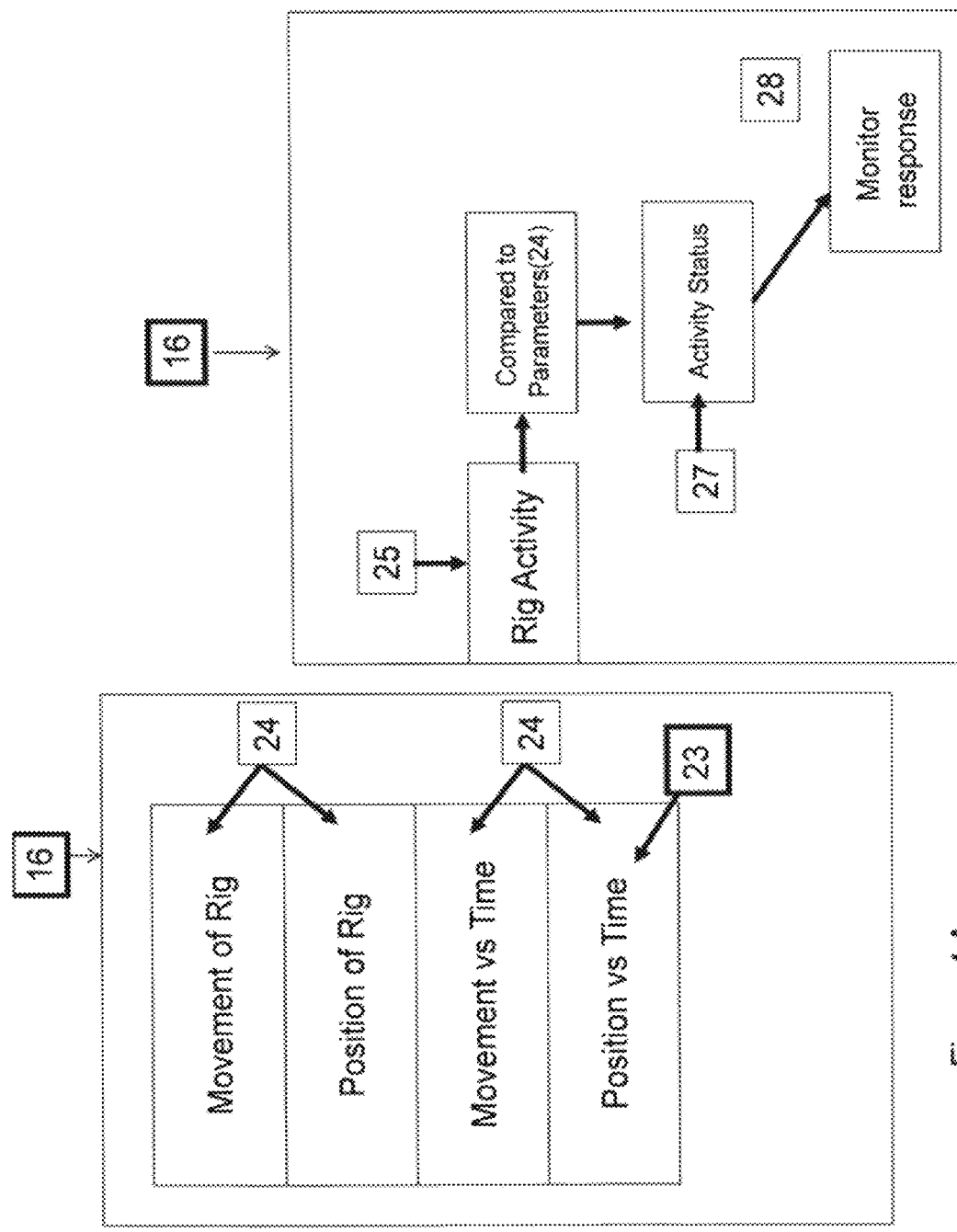
FIG. 4A is a schematic representation of the predetermined activity database of the controller of the system of FIG. 2.
FIG. 4B is a flow chart of the activity status assigning process of the controller of the system of FIG. 2.

As shown in FIG. 4A, the controller 16 comprises a database 23 of predetermined activity parameters 24. In an embodiment, the predetermined activity parameters 24 are allowable activity parameters. In one non-limiting example, the activity parameters relate to the (I) movement of the rig 20, the (II) position of the rig 20 within the map 22 and (Ill) time or the temporal parameters with respect to (I) and (II). As the rig 20 moves within the grid map 22 the controller 16 compares in real-time the rig's activity to the pre-determined allowable activity parameters.

Examples of activity parameters with respect to the (I) movement of the rig, include without limitation: (a) the stance of the rig (standing, slouching, kneeling, falling, lying down, sitting); (b) the walking gate of the rig; (c) the arm movement of the rig (e.g. reaching for support), (d) the velocity of the rig; and (e) the range of motion of the rig in relation to various body structure movements of the skeletal rig including without limitation: flexion, extension, abduction, adduction, rotation, medial rotation, lateral rotation, elevation, depression, pronation, supination, dorsiflexion, planarflexion, eversion, inversion, protrusion, retrusion, protraction, retraction, circumduction, apposition, reposition, reciprocal motion and any combination thereof.

Examples of activity parameters with respect to the (II) position of the rig include without limitation (a) the presence or absence of the rig within certain zones of the grid map, (b) the collision of the rig with individual obstructions (13) within the environment (14) (furniture, walls etc.); (c) the presence of the rig on or off certain objects within the map (e.g. bed, couch, bath etc.).

With respect to temporal parameters (III), activity parameters (I) and/or (II) can be dependent on a time range. Therefore, the presence or absence of the rig within certain zones or on/off certain objects within the map is dependent on a time range. For example, the rig should be on their bed between 9 pm and 7 am. Moreover, their position on the bed should be vertical (lying down). This activity can thus be classified under a normal activity status.

Therefore with respect to FIG. 4A, the various activities 25 FIG. 4B of the rig 20 are compared to the permutations of the parameters (I), (II) and (III) and as such an activity status 27 is assigned to a given activity and thereby a monitor response 28 is issued by the controller 168. In one example, shown in FIG. 6, the alarm monitoring activity statuses comprise of a range of status from (A) Normal, to (D) High Risk with the possibility of having graded risk levels such as (B) Low Risk, (C) Medium Risk. Time range is an important parameter as a Normal Status activity can be changed to High Risk status if the rig 20 is performing this activity for certain range at a time that is far greater than the predetermined normal time range. For example, a lying down position on the bed until 8am can still be classified as Normal, but one that lasts until 10am can be classified as Higher Risk. Assigning activities based on parameters (I), (II) and (III) depend on the behavior of the subject or the user's predetermined allowable behaviors as determined in the system set as will be further explained below. Therefore, the activity parameters can be tailored in order to assign statuses to the activities of a subject based on their range of daily behavior and their specific needs.

As such an activity is graded according to a risk (A, B, C, and D) above and then classified under a given activity status.

The controller 16 then communicates the activity status to a remote interface 18 for a remote user to ascertain the status of the subject H in real time. This interface 18 can be provided by a computer, a handheld device, an i-pod, an i-pad, a mobile phone, and smart phone and the like as the skilled artisan will easily contemplate. For High Risk Status activities the controller 16 can also signal an alarm (sound, voice, light etc) that is transmitted via the alarm device 19A of the interface 18 to the remote monitoring user or directly to the subject H by way of the alarm device 19B within the defined environment 14.

The Low and Medium Risk Statuses can be two components of a Warning Status, in which one lower status is differentiated from the medium status by a time period or proximity to a High Risk Status activity. As such, the controller 16 can also signal an alarm via the alarm device 19B in order to prevent an increase in the Risk Status.

Therefore, the systems and method of the disclosure provide for distinguishing between normal, abnormal, and dangerous activities, by performing a continuous 24h/7 day non-intrusive behavioral monitoring and collision detection and/or prevention outline.

Figure 5:
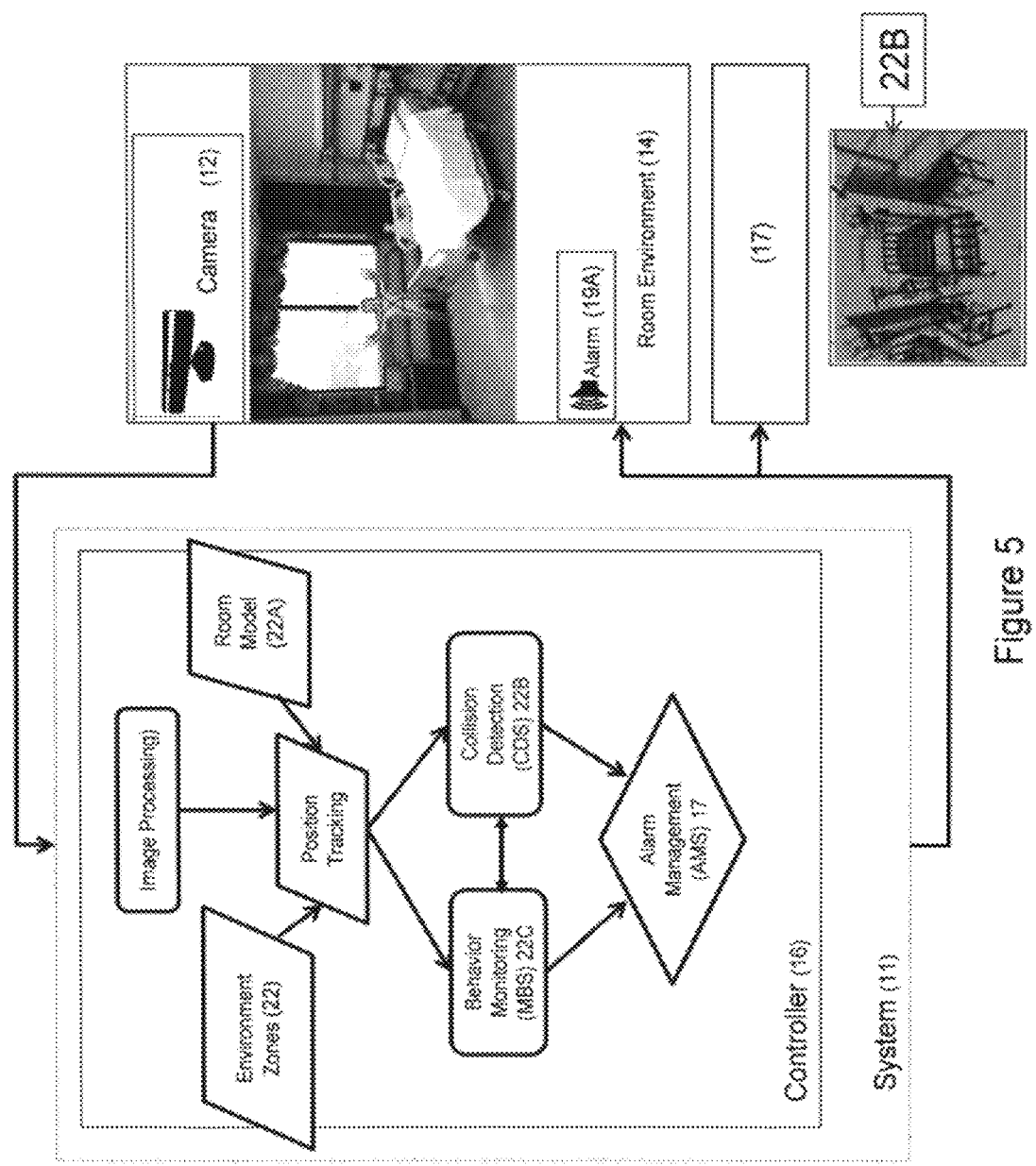
FIG. 5 is a schematic representation of the system for monitoring the activity status of a human subject within spatial and temporal parameters in accordance with another non-restrictive illustrative embodiment of the present disclosure.

More specifically, FIG. 5 provides a schematic representation of the system 11 for monitoring the activity status of a subject within spatial parameters in accordance with an embodiment of the present disclosure.

The system 11 includes a depth map camera 12' for monitoring a defined environment, such as a monitored subject's room 14'. The depth map camera 12' is in communication with a controller 16 that is linked to a monitoring station comprising an interface 18' (see FIG. 6) and an alarm output 19' positioned in the monitored room 14'.

The controller 16' provides for image processing of the images captured by the depth map camera 12' thereby building a grid map 22' based on two static data models: one model 22'A provides a virtual 3D representation of the room and the other model 22'B provides for describing the various zones in the room 14'. The computer models 22'A and 22'B are coupled with the video input of the depth map camera 12' thereby providing for real time Position Tracking 22'C of the subject H within the room 14'. Therefore, camera 12' also gathers subject H activity (i.e. "data depth information") and the field of vision of the camera 12' covers the areas within the environment 14' where subject H has access to.

The controller 16' also includes a Behavior Monitoring System (BMS) 22C for assessing the position of the subject H within the room via the position of the subject's rig 20 within the zoned grid map model 22'B and a Collision Detection System (CDS) for assessing the proximity of the subject H to an obstruction during movement within the virtual 3D grid map model 22'A. More specifically, the BMS and the CDS modulate an Alarm Management System (AMS) which is linked to the alarm output 19' and the display 18.

Therefore, the BMS and CDS will so modulate the AMS as to signal the activity status (or alarm) to the monitoring station, as soon as the subject H enters a danger zone, for example if is too close to furniture or a wall.

Before the system 11 can monitor the subject H within the room 14' and assess its activity status so as to signal an alarm or a report to the remote monitoring station the monitoring operation needs be properly parameterized beforehand by way of the following steps:

(1) recording the reference room 14' images;

(2) specifying the various periods of time where the subject H is allowed to be present within a certain zone of the room 14' during specific times of day;

(3) defining and recording the audio messages which will be transmitted to the subject H under specific predetermined circumstances. For example, if the subject H gets out of a safe zone (e.g. bed) during a certain time (normal sleep time) and moves into a warning zone, a pre-recorded audio message (using a familiar voice), is transmitted with a specific message, suggesting to the subject H to go back to bed;

(4) creating a computer representation such as a skeletal rig 20 of the subject H by calibrating the image and recording it for future usage;

(5) maintaining the parameter database of the subject H containing the information assessed in steps (1) to (4) accessible only by the monitoring station;

(6) creating a 3D virtual model 22'A of the room 14'; and (7) interactively determining zones in the room image 22'B representing the room at different intervals during specific times of day.

In one embodiment, there are three types of zones within the spatial parameters of the alarm grid regarding the physical position of the subject being monitored: a Safe Zone a Warning Zone and a Danger Zone.

The Safe Zone refers to an area or areas in which there is no apparent danger to the subject or the potential for a dangerous situation to occur. Typically this is the area of the room where the subject H can walk sit, or sleep. The Warning zone refers to an area or areas in a room adjacent the Safe Zone, and in which the subject H can stay for a certain period of time, without danger. It is expected that, after that period, the subject reintegrates into the Safe Zone. A non-limiting example of such a zone is the area in proximity to the floor of the room. For example, the subject H can kneel down, and return to an upright position after period of 30 seconds for example or as otherwise predetermined in the system set up as applicable to the subject being monitored. The Danger Zone refers to an area or areas within the room in which the subject H should not be present for more than 10 seconds. Of course, this time can be adjusted depending on the needs of the subject H. It is expected that after this period of time, the subject moves back into the Warning Zone. If this does not happen, an alarm is triggered and propagated to a remote device such as the monitoring station.

Once the above system set-up has been performed, the monitoring process can be initiated.

The BMS and the CDS run continuously (24/7) in order to track the activities of the subject H (via its rig 20). The system is constantly reviewing the data collected and alarms generated to refine the overall validity of the alarm monitoring system through the use of algorithms, and machine learning as will be understood by the skilled artisan.

The BMS determines in real time (30 fps), the position of the subject H and triggers an alarm as soon as certain conditions are met. For example the subject H falls down and stays in a pre-determined danger zone (during the day, the danger zone might be within a certain distance from the floor of the room), for more than a predetermined number of seconds. Due to the capacity of the system to continuously monitor the subject H, it can determine if a subject H is falling, or bending to pick up something on the floor. The CDS can also be activated at the same time as the BMS in order to monitor the subject's movements in 3D and provide alerts prior to intersecting with an object such as a piece of furniture in the room for instance.

Therefore, the computer models 22'A 22'B and 22'C provide for assigning activity statuses to various activities of the subject H and the BMS and CDS provide for assessing the rig activity and comparing this real time activity to the assigned statuses in order to transmit this information to the monitoring station and the alarm 19'.

Figure 6:
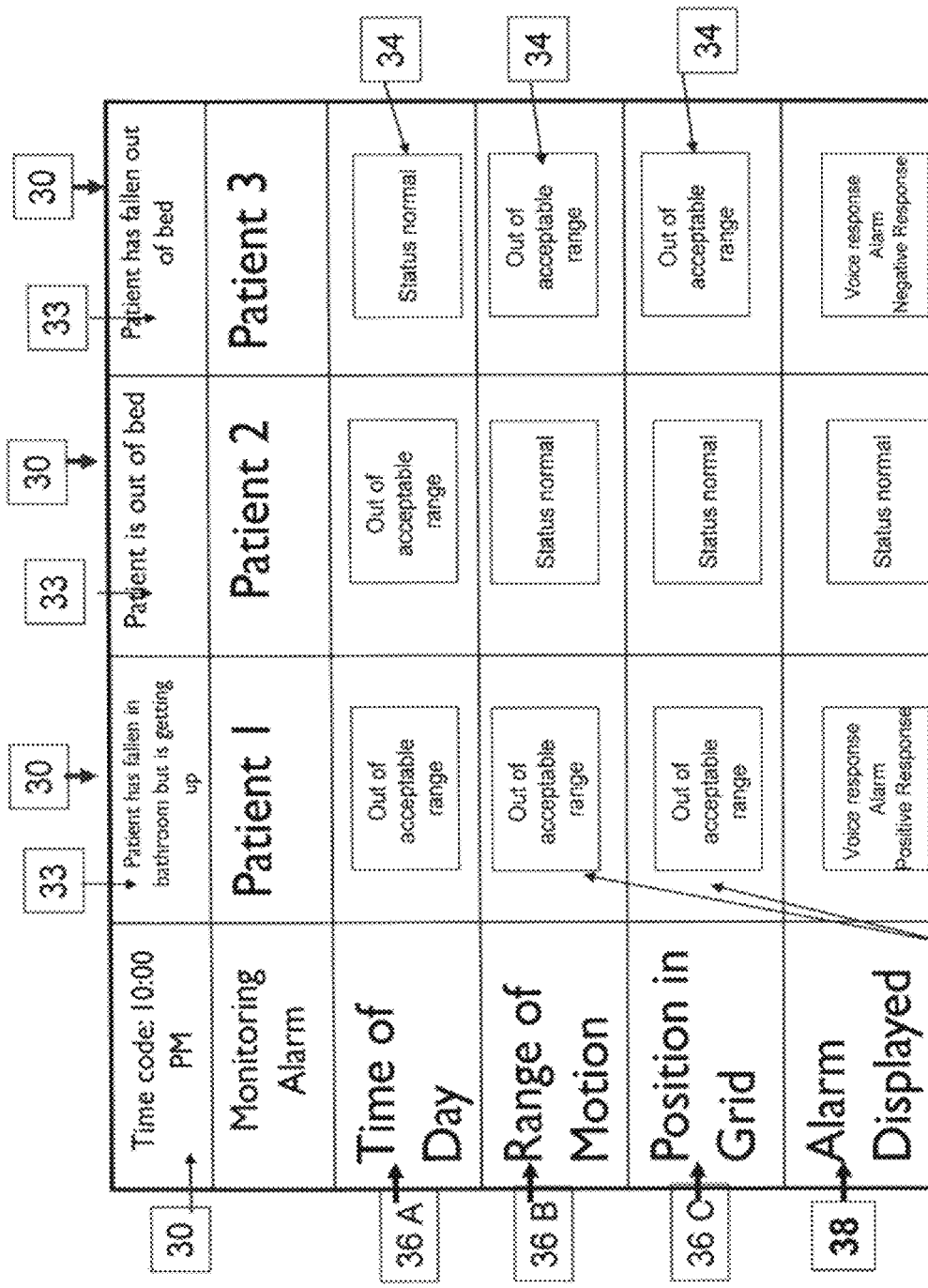
FIG. 6 is a schematic representation of an interface display of the system of FIG. 5.
Figure 7:
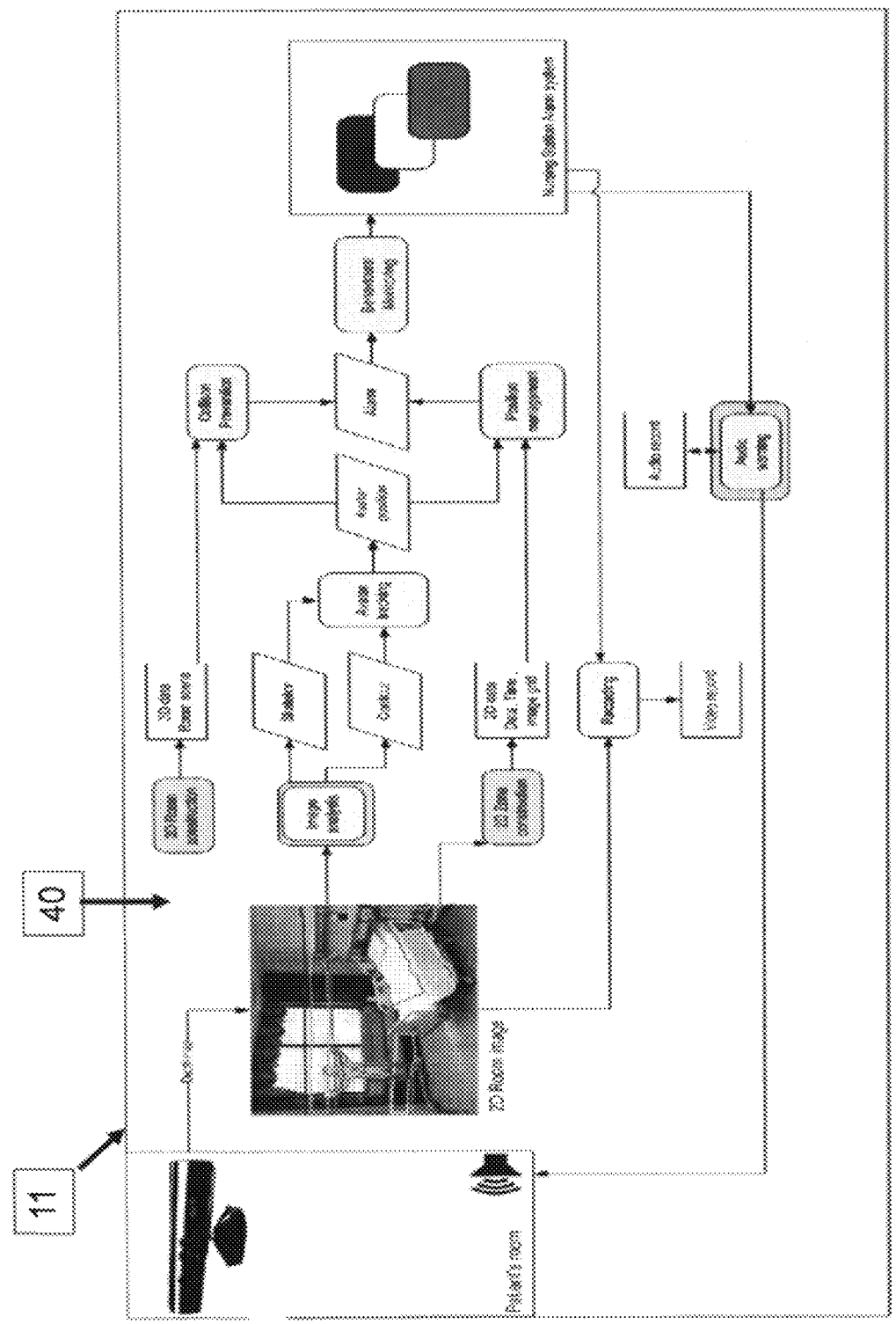
FIG. 7 is a schematic representation of the software modules and data structures of the system of FIG. 5.

With respect to FIG. 6, the interface 18' of the monitoring stationis represented in accordance to a non-restrictive illustrative embodiment. The monitoring station collects and displays (via the interface 18') the signals from the alarm management modules of the AMS. As is shown, the interface 18' provides for monitoring plurality of subjects which can be monitored via the system 11; these subjects are represented in columns 30 entitled clients 1, 2 and 3. As an example, the time 32 of day is recorded in real time and the actual actions 33 of the rig 20 displayed for each client column 30. Of course in another embodiment, the actions 33 are not displayed per se, and hence, reference 33 merely denotes herein the actions that have occurred and the rest of the interface 18' demonstrates how these actions are assessed by the system 1 in FIG. 7.

Therefore in one embodiment, without actually viewing the rig 20 let alone the actual subject H by way of video, a number of actual occurring rig activities are assigned descriptions which are displayed. If a given activity has not been assigned a description, the displayed action 33 can be "unknown" and a suitable alarm can be signaled. At this time, the interface can include a video display of the rig 20 or of the subject H as recorded in order for the remote user to assess the situation. Each displayed activity 33 is classified under an activity status 34 (for example "Normal" and "Out of acceptable range"). The status of an activity is determined for each parameter 36: Time of Day 36A, Range of Motion 36B and Position in Grid 36C. The aggregate of each status provided by the activity in view of the parameter results in a Monitoring Response 38 which is displayed when there is no response (thus a Normal aggregate status) or displayed signaled via an alarm when a response is needed (Out of Normal aggregate status). The procedure for the embodiment where activities 33 are not displayed but merely occur is similar.

Again, the interface 18' can include the option of selectively displaying the rig 20 within the virtual environment 14' or even the actual subject H as recorded when such viewing is ascertained as being necessary (and ascertained as having the appropriate privileges to view such activity).

It should be noted that the viewing of the real-time and historical capture of the data in the AMS can selectively be assigned hierarchical viewing privileges as determine in the system setup of users. As such, the range of data will span from being limited to viewing only alarm status display all the way down to viewing details in real-time of the rig/avatar data in its environmental context. There might be instances where users would need to view this history of a rig/avatars behaviour associated with the triggering of an alarm and where analysis of this data might lead to quality improvements in the environment.

It should also be noted that the AMS system can also collect and analyze alarm data in order to determine through artificial intelligence a set of repetitive behaviour patterns that could adjust the risk parameters in order to refine the alarm sensitivity. The risk grade of an activity is defined by the deviation from the behavioral norm using static or dynamic analysis with machine and human assisted learning as is understood by the skilled artisan With respect to FIG. 7, there will now be provided a general software 40 description of the system 11 in accordance with a non-restrictive illustrative embodiment of the present disclosure.

The system 11 comprises nine modules, one monitoring station 17 and eight types of data.

Functional Description of the Modules:
Image Analysis: detects the skeletal rig and the static objects of the scene. It contains the calibration system for skeleton recognition.
Initial Virtual Alarm Grid Construction: determines the various zones of the image, depending of the time of day and various other parameters using the depth map data or a 2D image from the 3D sensor and creates the environmental alarm area database, proper for each subject H.
Environment Construction (2D or 3D): recreates a virtual room.
Rig/Avatar Tracking: updates the subject's rig or avatar, the latter being constructed from 3D skeleton (skeletal rig) and the 2D contour, in real time (30 frames per second).
Position Management: tracks in real-time the position of the rig or avatar relative to the active grid map (virtual environment) and matches contour and skeleton data with the 2D image grid, according to the time of day. Using heuristic behavior to generate alarm signals when needed.
Behavioral Monitoring: transmits signals to the monitoring station 17 according to the alarms sent by the Position Management module to the Control Center (described below).
Collision Prevention: monitors the rig or the avatar's position in the 3D virtual environment and transmits signals to the monitoring station 17 depending on the rig's or avatar's proximity to an obstruction.
Audio Warning: transmits an automated and pre-recorded audio message to the subject's room, when potential danger may occur. The system 11 can also include an audio input connected with the monitoring station 17 for live interaction, through voice recognition software with the subject if required.
Video Recording: records the subject's behavior and it can be manually initiated.
Control center: this is the main module that manages the other seven modules.

Figure 8:
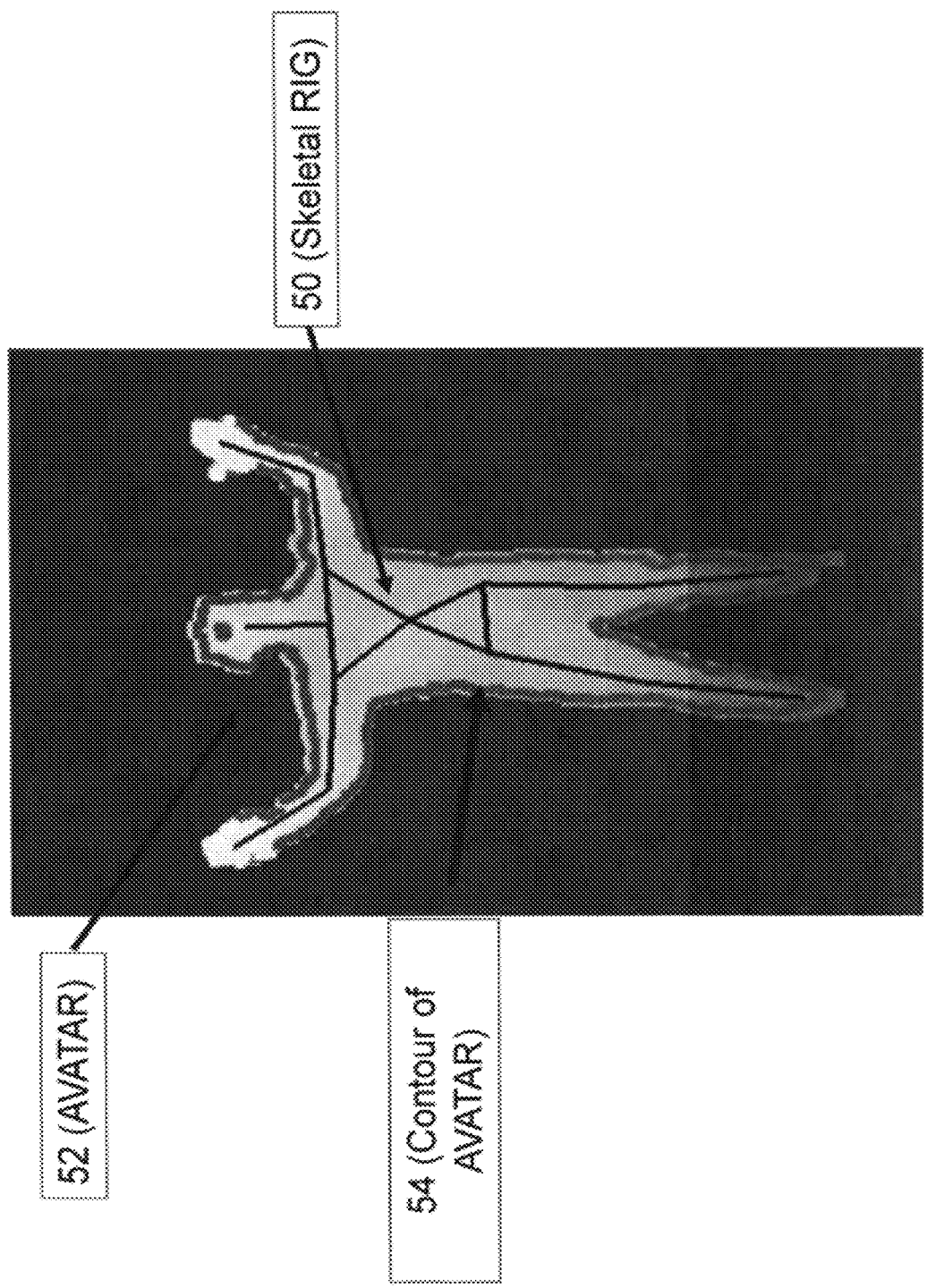
FIG. 8 is a schematic representation of an avatar and skeletal rig providing a virtual representation of the monitored human subject.

Description of Data Structures
The various formats of data which are needed during the two phases of the process (set-up and monitoring) will not be described.
Skeleton (skeletal rig) (denoted 50 in FIG. 8): 24 three-dimensional points describing the complete skeleton: head, neck torso, waist, plus left/right collar, shoulder, elbow, wrist, hand, fingertip, hip, knee ankle and foot (to the extent that the data can be pulled from the depth map).
Avatar Position: this compound object is made up of a contour and the corresponding skeleton thereby building an avatar 52 in FIG. 8.
Contour (54): a closed polyline surrounding the avatar.
3D Zoned Model: a 3D scene made of bounding boxes describing the room's allowed/forbidden zones.
2D Zoned Model: for each time zone, a colored grid describing the room's allowed/forbidden zones.
Alarm: the message data containing various information needed for the system 11.
Video Record: a video file with proper date and time and specific avatar IDs.
Audio record: an audio recording of pre-identified suggestions for the subject activated in light of an activity status.

Figure 9:
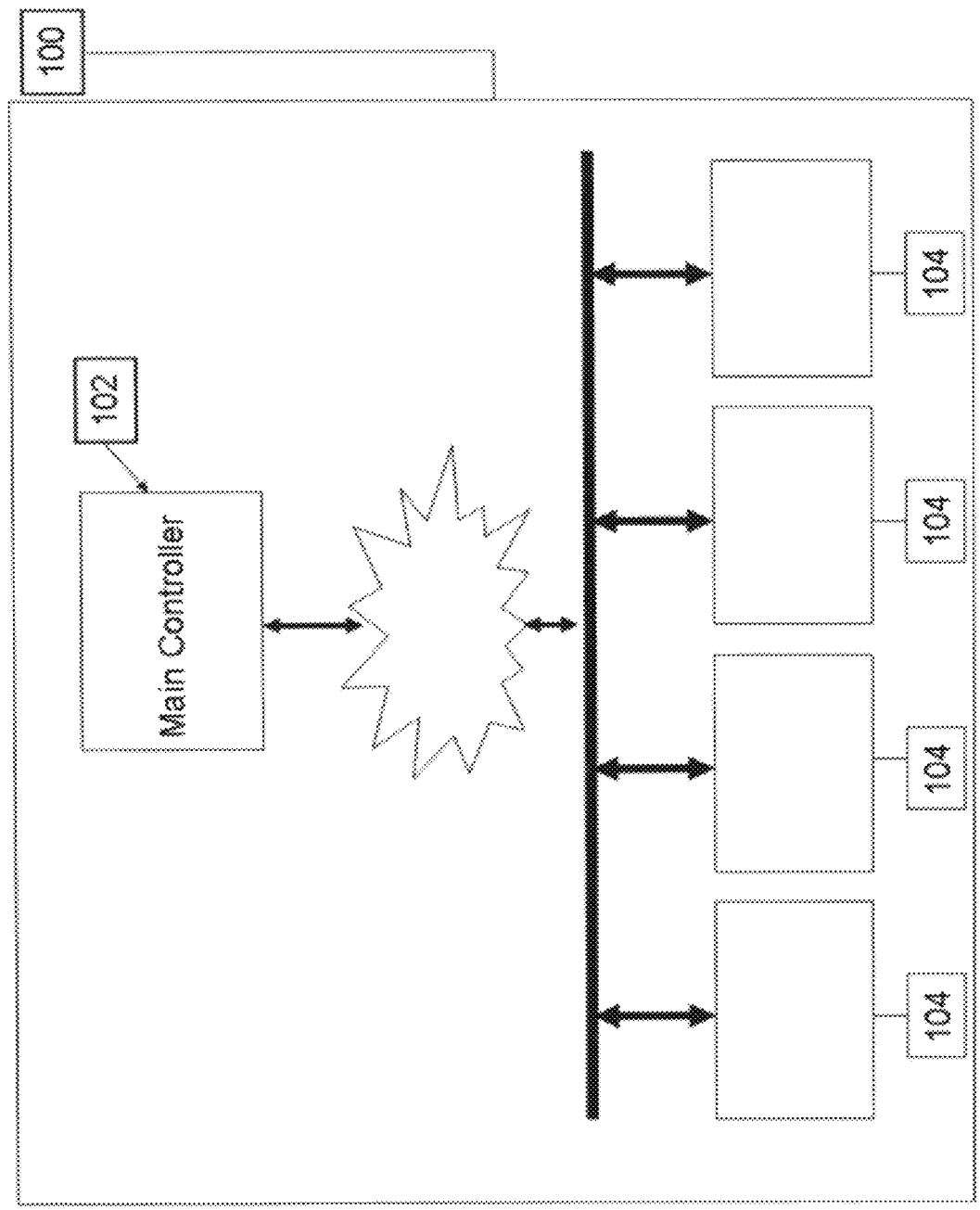
FIG. 9 is a schematic representation of a network providing for data accumulation from one or more systems for monitoring the activity status of a human subject within spatial, behavioral and temporal parameters.

Turning now to FIG. 9, there is shown a network 100 comprising a main controller 102 in communication with a plurality of controllers 104. Each controller 104 monitors one or more subjects H in one or more environments within one or more facilities. The main controller 102 receives data from each controller 104 related to the activity of each monitored subject as well as to the response time from signaling the remote user to redressing the situation. The main controller 104 also evaluates the success of the various in-room alarms in suggesting that the subject moves from a warning or danger zone to a safe zone. In essence, the overall operation of each system is assessed in order to provide data which can be used to improve response time and reduce the risk factors to the subject's well being.

The present disclosure is not limited in its application and implementation to the examples shown herein. As such, the present methods and systems can also be used in other activities other than monitoring patients. For example, monitoring at a distance the behavior of pets such as dogs and cats can also be contemplated. Other applications can include monitoring children in homes, schools or other facilities. The methods and systems provided herein can also be used for monitoring detained persons or even in work areas to assess dangerous situations.

It should be noted that the various components and features of the embodiments described above can be combined in a variety of ways so as to provide other non-illustrated embodiments within the scope of the disclosure. As such, it is to be understood that the disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been described hereinabove by way of embodiments thereof, it can be modified, without departing from the spirit, scope and nature of the subject disclosure as defined herein and in the appended claims.

What is claimed is:

1. A method of remotely monitoring physical movement activity of a patient suffering from dementia, the patient being placed within a defined spatial environment comprising a room including at least one furniture element therein, the room defining a living space for allowing the patient to freely move therein as desired, the method comprising:
(a) continuously capturing a real time image of the defined spatial environment;
(b) continuously translating in real time the captured image in (a) into a virtual 3-D model thereof;
(c) continuously capturing a real-time image of the patient throughout the environment without placing monitoring elements on the patient and without invasive physical or video observation of the patient so as to respect the privacy thereof within the environment;

(d) continuously translating in real time the captured image in (c) into a real-time 3-D avatar of the patient within the virtual 3-D model of the environment, wherein the real time physical activity of the patient throughout and in relation to the defined spatial environment is translated into real-time movement of the avatar throughout and in relation to the virtual 3-D model;

(e) providing continuous automated monitoring of the real time movement of the avatar within the virtual 3-D model without direct physical or video observation of the patient, the automated monitoring comprising:

assigning a given activity status to a movement of the avatar throughout and in relation to the virtual 3-D model which is a translation of a given physical movement activity of the patient throughout and in relation to the defined spatial environment thereby providing a computer memory of predetermined avatar activities classified according to an activity status codification, wherein assigning a given activity status to a movement of the avatar comprises grading the movement according to pre-determined behavioral parameters, wherein the pre-determined behavioral parameters of a movement of the avatar are dependent on the time of day, and the physical position of the patient throughout and in relation to the environment, wherein the virtual 3-D model is divided into zones, the presence of the avatar in a given zone is indicative of a given risk grade;

continuously assessing a real-time movement of the avatar throughout and in relation to the virtual 3-D model which is a translation of a physical movement activity of the patient throughout and in relation to the defined spatial environment; and continuously comparing in real-time the assessed movement of the avatar throughout and in relation to the virtual 3-D model with the predetermined avatar activities classified according to an activity status codification thereby continuously and automatically determining an activity status in real-time of the patient within the defined spatial environment; and transmitting in real time the determined activity status in (e) based on the activity status codification to a remote user thereby providing the remote user to ascertain the physical activity of the patient throughout and in relation to the environment without invasive physical or video observation of the patient so as to respect the privacy thereof within the environment.

2. A method according to claim 1, wherein signaling the real-time activity status comprises transmitting the determined activity status in real-time to the remote user.

3. A method according to claim 2, wherein transmitting the determined activity status in real-time to the remote user comprises transmitting an activity identifying signal to the remote user via a user interface.

4. A method according to claim 1, further comprising assigning a given alarm signal to a given activity status.

5. A method according to claim 4, further comprising transmitting the given alarm signal to the patient in real-time.

6. A method according to claim 4, further comprising transmitting the given alarm signal to the remote user in real-time.

7. A method according to claim 1, further comprising:
determining a set of repetitive behaviour patterns of the avatar during automated monitoring; and
adjusting the predetermined behavioural parameters based on the repetitive behaviour patterns.

8. A system of remotely monitoring physical movement activity of a patient suffering from dementia, the patient being placed within a defined spatial environment comprising a room including at least one furniture element therein, the room defining a living space for allowing the patient to freely move therein as desired, the system comprising:

at least one camera for continuously capturing a real time image of the defined spatial environment and continuously capturing a real-time image of the patient throughout the environment, a controller in communication with the camera for receiving in real-time the captured image of the environment and the patient, the controller continuously translating in real time the captured image of the environment into a virtual 3-D model thereof and continuously translating in real time the captured image of the patient into a real-time 3-D avatar thereof of within the virtual 3-D model of the environment, wherein the real time physical activity of the patient throughout and in relation to the defined spatial environment is translated into real-time movement of the avatar throughout and in relation to the virtual 3-D model, the controller providing for continuous automated monitoring of the real time movement of the avatar within the virtual 3-D model without direct physical or video observation of the patient so as to respect the privacy thereof within the environment, the controller comprises a memory of a plurality of predetermined activities classified according to an activity status codification, each activity status corresponding to a respective given movement of the avatar throughout and in relation to the virtual 3-D model which represents a given physical movement activity of the patient throughout and in relation to the defined spatial environment based on pre-determined behavioral parameters dependent on the time of day and the physical position of the patient throughout and in relation to the environment, wherein the virtual 3-D model is divided into zones, the presence of the avatar in a given zone is indicative of a given risk grade, the automated monitoring comprising the controller performing the steps of:

continuously assessing a real-time movement of the avatar throughout and in relation to the virtual 3-D model which is a translation of a physical movement activity of the patient throughout and in relation to the defined spatial environment; and continuously comparing in real-time the assessed movement of the avatar throughout and in relation to the virtual 3-D model with the predetermined avatar activities classified according to an activity status codification thereby continuously and automatically determining an activity status in real-time of the patient within the defined spatial environment; and a user interface in communication with the controller for receiving in real time the determined activity status based on the activity status codification thereby providing a remote user to ascertain the physical activity of the patient throughout and in relation to the environment without invasive physical or video observation of the patient so as to respect the privacy thereof within the environment.

9. A system according to claim 8, further comprising an alarm device being in communication with the controller and being positioned within the environment for receiving the determined activity status and producing a predetermined signal associated with the determined activity status.

10. A system according to claim 9, further comprising a remote alarm device in communication with the controller and being positioned at the user interface for receiving the determined activity status and producing a predetermined signal associated with the determined activity status.

11. An information processing system comprising:
a main controller; and
a plurality of monitoring systems according to claim 8 wherein each controller thereof is in communication with the main controller for transmitting information regarding: (a) the assessment of the real-time determined activity status of the patient within the environment, (b) the receipt of the determined activity status by the interface and (C) any response to a determined activity status.

* * * * *